(12) United States Patent
Sun et al.

(10) Patent No.: US 6,918,765 B1
(45) Date of Patent: Jul. 19, 2005

(54) HYDROGEL DENTAL ADHESIVE COMPOSITION, PRODUCT, SYSTEM, METHOD AND DISPENSER

(75) Inventors: Benjamin J. Sun, York, PA (US); Andrew M. Lichkus, York, PA (US)

(73) Assignee: Dentsply Research & Development Corp.

( * ) Notice: Subject to any disclaimer, the term of this patent is extended or adjusted under 35 U.S.C. 154(b) by 100 days.

(21) Appl. No.: 10/171,736

(22) Filed: Jun. 14, 2002

Related U.S. Application Data

(63) Continuation of application No. 09/488,078, filed on Jan. 20, 2000, now abandoned.
(60) Provisional application No. 60/117,100, filed on Jan. 25, 1999.

(51) Int. Cl.$^7$ .................. A61C 13/02; A61C 13/225
(52) U.S. Cl. ............... 433/168.1; 433/180; 523/120
(58) Field of Search ............... 433/168.1, 180; 523/180, 120

(56) References Cited

U.S. PATENT DOCUMENTS

| | | | |
|---|---|---|---|
| 3,628,988 A | 12/1971 | Stol et al. .................. 117/63 |
| 3,674,901 A | 7/1972 | Shepard et al. ............... 424/27 |
| 3,745,651 A * | 7/1973 | Hofacker et al. ............ 433/172 |
| 3,787,231 A | 1/1974 | Lebel et al. ............. 117/138.8 |
| 3,849,185 A | 11/1974 | Shepard et al. ............. 117/161 |
| 3,881,026 A | 4/1975 | Shepard et al. ............. 426/223 |
| 3,930,076 A | 12/1975 | Kliment ..................... 427/353 |
| 3,939,123 A | 2/1976 | Matthews et al. ......... 260/77.5 |
| 3,940,542 A | 2/1976 | Knopf et al. ............... 428/364 |
| 3,941,858 A | 3/1976 | Shepherd et al. ........... 260/885 |
| 4,202,098 A | 5/1980 | Russo ....................... 433/168 |
| 4,239,488 A | 12/1980 | Sempler .................... 433/180 |
| 4,367,732 A | 1/1983 | Poulsen et al. ............ 128/156 |
| 4,373,036 A | 2/1983 | Chang et al. ............... 523/120 |
| 4,379,864 A | 4/1983 | Gallop et al. .............. 523/106 |
| 4,469,477 A | 9/1984 | Potter ....................... 433/168 |
| 4,485,090 A | 11/1984 | Chang ........................ 424/52 |
| 4,503,116 A | 3/1985 | Lapidus ..................... 428/286 |
| 4,514,528 A | 4/1985 | Dhabhar et al. ............ 523/120 |
| 4,521,551 A | 6/1985 | Chang et al. ............... 523/120 |
| 4,522,956 A | 6/1985 | Dhabhar et al. ............ 523/120 |
| 4,530,942 A | 7/1985 | Dhabhar et al. ............ 523/118 |
| 4,543,371 A | 9/1985 | Gallop et al. .............. 523/106 |
| 4,599,216 A | 7/1986 | Rohrer et al. ................ 422/21 |
| 4,632,880 A | 12/1986 | Lapidus ..................... 428/523 |
| 4,828,493 A | 5/1989 | Nambu et al. ............ 433/199.1 |
| 4,867,748 A | 9/1989 | Samuelsen .................. 604/336 |
| 4,920,203 A | 4/1990 | Tang et al. .................. 525/409 |
| 5,033,486 A | 7/1991 | Finamore et al. ........... 132/201 |
| 5,034,461 A | 7/1991 | Lai et al. .................... 525/100 |
| 5,066,772 A | 11/1991 | Tang et al. .................. 528/354 |
| 5,073,604 A | 12/1991 | Holeva et al. ............ 525/327.8 |
| 5,115,801 A | 5/1992 | Gartmell et al. ............. 602/48 |
| 5,152,781 A | 10/1992 | Tang et al. .................. 606/230 |
| 5,178,851 A | 1/1993 | Gaffar et al. ................. 424/52 |
| 5,180,578 A | 1/1993 | Gaffar et al. ................. 474/52 |
| 5,188,821 A | 2/1993 | Gaffar et al. ................. 424/52 |
| 5,192,530 A | 3/1993 | Gaffar et al. ................. 424/52 |
| 5,258,421 A | 11/1993 | Lorenz et al. ............... 523/111 |
| 5,274,074 A | 12/1993 | Tang et al. .................. 528/370 |
| 5,288,480 A | 2/1994 | Gaffar et al. ................. 424/52 |
| 5,292,526 A | 3/1994 | Gaffar et al. ................. 424/49 |
| 5,294,431 A | 3/1994 | Gaffar et al. ................. 424/49 |
| 5,306,504 A | 4/1994 | Lorenz ....................... 424/449 |
| 5,312,618 A | 5/1994 | Gaffar et al. ................. 424/52 |
| 5,316,774 A | 5/1994 | Eury et al. .................. 424/501 |
| 5,334,691 A | 8/1994 | Gould et al. ................. 528/76 |
| 5,344,641 A | 9/1994 | Gaffar et al. ................. 424/49 |
| 5,420,197 A | 5/1995 | Lorenz et al. ............. 525/54.3 |
| 5,424,058 A | 6/1995 | Rajaiah et al. ............... 424/49 |
| 5,453,265 A | 9/1995 | Gaffar et al. ................. 424/52 |
| 5,466,437 A | 11/1995 | Gaffar et al. ................. 424/52 |

(Continued)

OTHER PUBLICATIONS

Razavi et al, Journal of Prosthodontics, vol. 2, No. 4 (Dec.), 1993: pp 224–227; Clinical Applications of a Polyphosphazene–Based Resilient Denture Liner.

Primary Examiner—Cary E. O'Connor
(74) Attorney, Agent, or Firm—Daniel W. Sullivan; James B. Bieber; Douglas J. Hura

(57) ABSTRACT

A dental product formed by a process and a method of using a denture including providing a denture having an outer face, applying a readily flowable material to the face. The flowable material comprises volatile material and polymeric material. Volatilizing at least a portion of the volatile material from the flowable material to form a readily peelable water swellable solid film. The film is substantially insoluble in water. The film comprising at least 10% by weight of the polymeric material. The denture having an outer face. The film adheres to the face and film effectively not being covalently bonded to the face. The product and method are preferably carried out using an adhesive dispenser including a container, a pump and flowable adhesive. The flowable adhesive is enclosed by the container. The pump is supported by the container and the pump is connected through a conduit to the flowable adhesive. A preferred flowable composition includes at least 1% volatile organic material, at least 10% by weight water, and at least 10% by weight polymeric material. The polymeric material comprising a compound within the scope of

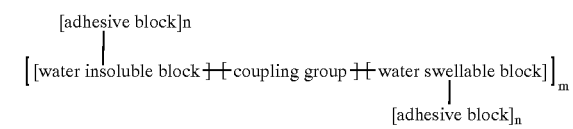

wherein m is an integer from 3 to 1,000 and each n independently is an integer from 0 to 100.

11 Claims, No Drawings

U.S. PATENT DOCUMENTS

| | | | |
|---|---|---|---|
| 5,486,593 A | 1/1996 | Tang et al. | 528/370 |
| 5,489,427 A | 2/1996 | Bilbrey | 424/76.6 |
| 5,525,652 A | 6/1996 | Clarke et al. | 524/37 |
| 5,538,715 A | 7/1996 | Gaffar et al. | 424/52 |
| 5,539,039 A | 7/1996 | Kwak et al. | 524/401 |
| 5,540,033 A | 7/1996 | Fox et al. | 53/425 |
| 5,543,443 A | 8/1996 | Rajaiah et al. | 523/120 |
| 5,561,177 A | 10/1996 | Khaledi et al. | 524/35 |
| 5,571,080 A | 11/1996 | Jensen | 602/56 |
| 5,575,652 A | 11/1996 | Gaffar et al. | 433/173 |
| 5,624,745 A | 4/1997 | Lapidus | 428/308.8 |
| 5,645,855 A | 7/1997 | Lorenz | 424/449 |
| 5,658,586 A | 8/1997 | Rajaiah et al. | 424/435 |
| 5,674,275 A | 10/1997 | Tang et al. | 607/152 |
| 5,686,064 A | 11/1997 | Gaffar et al. | 424/57 |
| 5,696,181 A | 12/1997 | Chang et al. | 523/118 |
| 5,704,905 A | 1/1998 | Jensen et al. | 602/58 |
| 5,728,756 A | 3/1998 | Gaffar et al. | 524/139 |
| 5,731,365 A | 3/1998 | Engelhardt et al. | 523/206 |
| 5,744,180 A | 4/1998 | Cherukuri et al. | 426/99 |
| 5,750,591 A * | 5/1998 | Clarke et al. | 523/120 |
| 5,760,102 A | 6/1998 | Hall et al. | 523/120 |
| 5,763,682 A | 6/1998 | Moore | 568/672 |
| 5,776,435 A | 7/1998 | Gaffar et al. | 424/49 |
| 5,776,493 A | 7/1998 | Barclay et al. | 424/468 |
| 5,824,342 A | 10/1998 | Cherukuri et al. | 424/484 |
| 5,869,096 A | 2/1999 | Barclay et al. | 424/468 |
| 5,872,160 A | 2/1999 | Liang et al. | 528/120 |
| 5,877,233 A | 3/1999 | Liang et al. | 523/120 |
| 5,880,172 A | 3/1999 | Rajaiah et al. | 523/120 |
| 5,885,829 A | 3/1999 | Mooney et al. | 435/325 |

* cited by examiner

HYDROGEL DENTAL ADHESIVE COMPOSITION, PRODUCT, SYSTEM, METHOD AND DISPENSER

This application is a continuation of application Ser. No. 09/488,078, filed Jan. 20, 2000 now abandoned, which claims benefit of U.S. patent application Ser. No. 60/117,100 filed Jan. 25, 1999.

The invention relates to dental adhesives. The invention provides a hydrogel dental adhesive composition, product, system, method and dispenser. The invention provides a hydrogel denture adhesive and cushioning system for daily use on dentures. Hydrogel dental adhesive effectively holds dentures in place and also provides comfortable cushion for the denture. The thickness of the hydrogel denture adhesive solid film formed on the denture base is applied as a flowable hydrogel. In the mouth flowable hydrogel forms a solid film. The continuity and integrity of the denture adhesive solid film is maintained under physiological conditions of the user's mouth.

The invention provides new thermoplastic hydrophilic polymers that form hydrogels in water. Specifically, this invention provides a hydrogel based denture adhesive and thermoplastic hydrophilic polymer system that effectively holds dentures in place, allows for easy removal of the denture on demand and effectively provides comfort as a denture cushion. More importantly, this invention provides true hydrogel based daily use products for denture wearers. This invention utilizes the advantages of the hydrogels to prepare disposable denture adhesive/cushion devices (hydrogel based denture adhesive/cushion for daily replacement). This device is able to swell upon the absorbance of water and provide a soft cushion with highly flowable thermoplastic hydrogel that can fit voids and adjust thickness according to the imposed force (bite). A disposal denture adhesive/cushion device prepared from hydrogels in this invention contains 50 to 90 percent of water. The hydrogels of this invention are either a highly flowable gel under pressure or cured in situ to adapt the shapes between oral cavity and denture.

Prior art denture adhesives require spreading and removal of paste. Beneficially denture adhesive in accordance with the invention may be quickly and evenly applied to a denture by spraying. Beneficially all or at least a substantial portion of the denture adhesive applied to a denture in accordance with the invention may be quickly and easily removed from the denture by peeling as a continuous flexible solid film.

The flowability of this hydrogel system distinguishes it from other common hydrogels. This class of thermoplastic hydrogel is based on Pluronics, ε-caprolactone (or and glycolide, etc.) and diisocyanates (or other coupling agents).

The unique characteristics of this highly flowable hydrogel system provide numerous applications in medical, surgical and pharmaceutical industries. Its unique properties enable hydrogel compositions of the invention to adapt any shape to be applied by injection and/or spray and optionally provides controlled release devices as drug carriers, used in the form of flexible solid hydrogel layer.

Denture as used herein refers to dental prosthesis having a plurality of artificial teeth supported by a base, and adapted to be inserted into and removable from the mouth of a user by that user.

Gel as used herein refers to a colloid in which the disperse phase has combined with the continuous phase to form a viscous product.

Hydrogel as used herein refers to polymeric material which has absorbed water to form a gel.

Flowable as used herein refers to material which is adapted to move as a fluid under applied pressures preferably in the range of 0.1 psi to 500 psi.

Peelable as used herein refers to a layer which is readily peeled from the adjacent substrate and which is effectively not covalently bonded to the adjacent substrate.

It is also the object of the invention to provide a method of using a denture comprising providing a denture having an outer face, applying a readily flowable gel to the face, the gel comprising volatile material and polymeric material, volatilizing at least a portion of the volatile material from the gel to form a soft adhesive readily peelable water swellable solid film, the film being substantially insoluble in water, the film comprising at least 10% by weight of the polymeric material.

It is also the object of this invention to provide a dental product formed by a process comprising providing a flowable gel, and applying the gel to a surface of a denture, forming the gel into a soft adhesive readily peelable water swellable solid film, the film comprises at least 10% by weight of polymeric material, the film being substantially insoluble in water.

It is also the object of this invention to provide a dental product comprising a denture, and a soft adhesive readily peelable water insoluble, water swellable solid film, the film comprises at least 10% by weight of polymeric material, the denture having an outer face, the film adhering to the face and film effectively not being covalently bonded to the face.

It is also the object of this invention to provide a dental adhesive system, comprising: a denture and an adhesive dispenser, comprising a container, a pump, and flowable gel adhesive, the flowable gel adhesive being enclosed by the container, and the pump being supported by the container and extending into the flowable gel adhesive.

Unless otherwise indicated all percentages herein are percent by weight.

BRIEF SUMMARY OF THE INVENTION

A dental product formed by a process and a method of using a denture including providing a denture having an outer face, applying a readily flowable material to the face. The flowable material comprises volatile material and polymeric material. Volatilizing at least a portion of the volatile material from the flowable material to form a soft adhesive readily peelable water swellable solid film. The film is substantially insoluble in water. The film comprising at least 10% by weight of the polymeric material. The denture having an outer face. The film adheres to the face and film effectively not being covalently bonded to the face. The product and method are preferably carried out using an adhesive dispenser including a container, a pump and flowable adhesive. The flowable adhesive is enclosed by the container. The pump is supported by the container and the pump is connected through a conduit to the flowable adhesive. The polymeric material comprising a compound within the scope of

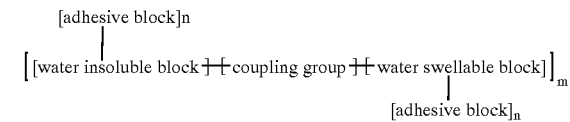

wherein m is an integer from 3 to 1,000 and each n independently is an integer from 0 to 100.

DETAILED DESCRIPTION OF THE INVENTION

A preferred embodiment of the invention provides a dental adhesive dispensing system including a dispenser container enclosing dental film forming adhesive. A pump is connected by a conduit to the adhesive. The conduit extends through upper surface of the adhesive. A nozzle is in fluid flow communication with the film forming adhesive through the conduit and the pump. Adhesive is sprayed as spray from the nozzle onto a face of a denture to form a coating on a coated face of the denture. Artificial teeth are supported by the denture opposite from the coated face.

The dental adhesive and spray are each a viscous liquid. Initially, volatile organic solvent volatilizes from coating to form a gel. Then a portion of the water in the gel volatilizes to form an adhesive film. Thus, the denture adhesive and cushioning system provided has three physical forms: film, gel and viscous liquid.

Preferably dental adhesive and spray are a viscous liquid mixture of polymer, water and volatile material, such as ethanol. Preferably, dental adhesive and spray each includes from 40 to 98% by weight water. Dental adhesive and spray initially are viscous liquid mixtures. Preferably these liquid mixtures include thermoplastic hydrophilic polymer within the scope of formula I and water. This viscous liquid rapidly forms a gel as ethanol volatilizes from the spray and coating. The gel is highly flowable and deformable, but insoluble in water. The weight percent of water in the gel is preferably from 50 to 90%. The gel forms into a strong, elastic, soft and resilient hydrogel film on the denture as a portion of the water volatilizes over an extended period of time. The amount of water in the resilient hydrogel film is preferably from 1 to 30 percent by weight of the film.

Film is soft, resilient, elastic and flexible in dry state. In hydrated state, film not only is soft, resilient, elastic and flexible, but also is flowable, highly pliable and deformable. Film is insoluble in water, and preferably includes a hydrophilic polymer. Preferably, film includes water and polymer in equilibrium state as a hydrogel containing from about 5 to about 60 weight percent of water.

In accordance with a preferred embodiment of the invention adhesive 14 includes water, ethanol (a volatile organic material) and multi-block hydrophilic thermoplastic copolymers within the scope of the general formula I:

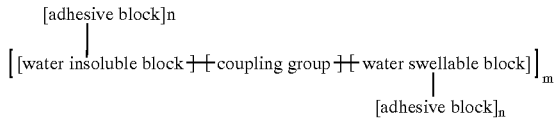

(I)

wherein m is an integer from 3 to 1,000 and each n independently is an integer from 0 to 100. Thus, formula I includes water swellable blocks and water insoluble blocks coupled by coupling groups.

Preferred compounds within the scope of formula I for use in accordance with the invention include 60 to 90% by weight of water insoluble block, 8 to 38% by weight water swellable block, 2 to 4% by weight coupling group and 0 to 20% by weight adhesive block.

Preferred compounds within the scope of formula I for use in accordance with the invention include 60 to 90% by weight of blocks formed from block copolymers of ethylene oxide and propylene oxide, 8 to 38% by weight ε-caprolactone, 2 to 4% by weight diisocyanate and 0 to 20% by weight sodium alginate.

Preferred water insoluble blocks for use within formula I include ethylene oxide-propylene oxide copolymer. Preferred water insoluble blocks for use within formula I have average molecular weights of from 1,000 to 20,000. For example preferred water insoluble blocks for use within formula I include ethylene oxide-propylene oxide copolymer, having average molecular weights of from 1,000 to 20,000 such as Pluronic F68NF (sold by BASF), Pluronic F108NF (sold by BASF), Pluronic F127NF (sold by BASF), Pluronic F38NF (sold by BASF), etc. Preferably the weight percent of water insoluble blocks in compounds within the scope of formula I is from about 49 to about 99.

Preferred water swellable polymer blocks are formed from monomers, oligomers or prepolymers such as ε-caprolactone. Optionally these monomers, oligomers or prepolymers are specifically substituted by from about 1 to 100 percent glycolide. Preferably, the weight percent of water swellable blocks in compounds within the scope of formula I is from 0.05 to about 50. Preferred water swellable blocks for use within formula I include ε-caprolactone. The following are useful as water swellable block copolymers in compounds within the scope of formula I for use in accordance with the invention: ε-caprolactone; hydroxyl-terminated poly(ε-caprolactone)s; hydroxyl-terminated polyesters; hydroxyl-terminated polyethers; isocyanate-terminated prepolymers; glycolide; lactide; bioabsorbable anhydrides; bioabsorbable monomers, oligomers and prepolymers; stannous chloride dihydrate; and dibutyltin dilaurate.

Preferably, the weight percent of coupling groups in compounds within the scope of formula I is from about 1 to about 5 percent. Preferred coupling groups for use within formula I include diisocyanates. Diisocyanates preferably used as coupling groups are substituted by anhydrides, bis(trimethylene carbonate), bis(ε-caprolactone), diacid and/or other coupling agents.

From 0 to about 30 weight percent sodium alginate is preferably included in compositions in accordance with a preferred embodiment of this invention as water activated adhesive.

Block copolymers of ethylene oxide and propylene oxide are relatively non-toxic and non-irritating. Preferred polymers for use as water insoluble blocks in the compounds of formula I for use in hydrogels of the invention include block copolymers of ethylene oxide and propylene oxide, such as Pluronic F68NF (sold by BASF) (the molecular weight of this block copolymer is 8400 with 80% of ethylene oxide and 20% of propylene oxide); Pluronic F127NF (the molecular weight of this block copolymer is 12600 with 70% of ethylene oxide and 30% of propylene oxide); Pluronic F108NF (the molecular weight of this block copolymer is 14600 with 80% of ethylene oxide and 20% of propylene oxide); Pluronic F38NF (the molecular weight of this block copolymer is 4700 with 80% of ethylene oxide and 20% of propylene oxide); Pluronic F87NF (the molecular weight of this block copolymer is 8400 with 70% of ethylene oxide and 30% of propylene oxide).

Preferred hydrophilic polymers for use as water swellable blocks in making water swellable polymers of formula I include: trimethyl-1,6-diisocyanatohexane; 1,6-diisocyanatohexane; 1,8-diisocyanatooctane; and Isophorone diisocyanate Organic diisocyanates are useful as water swellable polymers in compounds within the scope of formula I for use in accordance with the invention. Coupling agents with bifunctional groups of acids, anhydrides, caprolactone, carbonates, cyclic esters, lactones, epoxides, amines are useful as chain extenders to increase the molecular weight of thermoplastic polymers in accordance with the invention.

A preferred embodiment of the invention provides a hydrogel having biologically active agents. The hydrogel has the capacity for "controlled release" of biologically active agents. Preferred biologically active agents include flavors, antiseptic agents, germicidal agents, antifungal agents, antioxidants, antiseptic agents, odor masking agents, dental desensitizers, antibacterial agents, immune reagents, antibiotics, anti-inflammatory agents, anesthetics, nutritional agents, complexing agents, peroxides, a mixture of any of them and the like.

A preferred embodiment of the invention provides a hydrogel spray for dental, surgical, pharmaceutical and medical use, such as denture adhesive, anti-adhesion barrier, wound dressing material, skin burn dressing, cosmetic coating, coating for surgical and medical uses, and sprayable controlled release uses.

A preferred flowable composition includes at least 1% volatile organic material, at least 10% by weight water, and at least 10% by weight polymeric material.

EXAMPLE 1

Preparation of Block Copolymer of Poly(ethylene Oxide/propylene Oxide) (Pluronic F68NF) and ε-caprolacton, Coupled by Trimethyl-1,6-diisocyanatohexane A suitable flask was thoroughly cleaned, oven-dried and charged with 22.0 g (0.0026 mol) dried Pluronic F68NF under dry nitrogen flow. The flask was placed in an oil bath with a magnetic stirrer and the oil bath was heated to 70° C. under a positive nitrogen pressure. Comonomer ε-caprolactone (7.4 g, 0.065 mol) and catalyst stannous chloride dihydrate (0.10 g, 4.4×10$^{-1}$ mol) were charged into this reactor under constant stirring. Then the temperature of the oil bath was raised to 190° C. and maintained from 169 to 187° C. for 5 hours. To this opaque viscous intermediate product, added 0.32 g (0.0015 mol) of trimethyl-1,6-diisocyanatohexane. After 30 minutes, additional 0.40 g (0.0019 mol) of trimethyl-1,6-diisocyanatohexane was added over a period of 5 minutes. Three hours later, the heat was turned off and the flask was removed and block copolymer of poly(ethylene oxide/propylene oxide) and ε-caprolacton, coupled by trimethyl-1,6-diisocyanatohexane was collected and stored in a dry atmosphere.

EXAMPLE 2

Preparation of Block Copolymer of Poly(ethylene Oxide/propylene Oxide) (Pluronic F68) and ε-caprolactone, Coupled by Trimethyl-1,6-diisocyanate A suitable flask was thoroughly cleaned, oven-dried and charged with 70.0 g (0.0083 mol) dried Pluronic F68NF under dry nitrogen flow. The flask was placed in an oil bath with a magnetic stirrer and the oil bath was heated to 72° C. under a positive nitrogen pressure. Comonomer ε-caprolactone (46 g, 0.40 mol) and catalyst stannous chloride dihydrate (0.23 g, 1.0×10$^{-3}$ mol) were charged into this reactor under constant stirring. Then the temperature of the oil bath was raised to 162° C. and maintained about 160° C. for 3 hours. This reaction mixture was placed in vacuum oven overnight and unreacted ε-caprolactone was removed. Then the oil bath was heated to 192° C. and maintained from 168 to 192° C. for 1 hours. To this opaque viscous intermediate product, added 0.82 g (0.0039 mol) of trimethyl-1,6-diisocyanatohexane. After 12 minutes, 0.72 g (0.0034 mol) of trimethyl-1,6-diisocyanatohexane was added. About 12 minutes later, additional 0.75 g (0.0036 mol) of trimethyl-1,6-diisocyanatohexane was added 1.6 hour later, the heat was turned off and the flask was removed and block copolymer of poly(ethylene oxide/propylene oxide) and ε-caprolactone, coupled by trimethyl-1,6-diisocyanate was collected and stored in a dry atmosphere.

EXAMPLE 3

Preparation of Block Copolymer of Poly(ethylene Oxide/propylene Oxide) (Pluronic F127) Coupled by Trimethyl-1,6-diisocyanate A suitable flask was thoroughly cleaned, oven died and charged with 29.4 g (0.0020 mol) dried Pluronic F127 under dry nitrogen flow. The flask was placed in an oil bath with a magnetic stirrer and heated to 160° C. under a positive nitrogen pressure. Comonomer ε-caprolactone (6.0 g, 0.59 mol) and catalyst stannous chloride dihydrate (0.05 g, 2.2×10$^{-4}$ mol) were charged into this reactor under constant stirring. Then the temperature of the reactor was raised to 195° C. and maintained from 180 to 200° C. for 4 hours. The flask was removed and block copolymer of poly(ethylene oxide/propylene oxide) Pluronic F127 coupled by trimethyl-1,6-diisocyanate was isolated and stored in a dry atmosphere.

EXAMPLE 4

Hydrogel Denture Adhesive Films

Film-type hydrogel denture adhesive is prepared by blending 90 g of block polymer formed by following the procedure of Example 2 and 10 g of Sodium alginate.

The film-type hydrogel denture adhesive is stored in a flexible tube container. The user squeezes the tube to force adhesive onto the back of a denture. The user spreads the adhesive to form a coating on the denture. The user places the denture in the user's mouth. The coating forms a peelable film shaped to the user's mouth.

EXAMPLE 5

Hydrogel Denture Adhesive Gels

Gel-type hydrogel denture adhesive is prepared by mixing 20 g of copolymer prepared by following the procedure of Example 2 and 80 g of water.

The film-type hydrogel denture adhesive is stored in a flexible tube container. The user squeezes the tube to force adhesive onto the back of a denture. The user spreads the adhesive to form a coating on the denture. The user places the denture in the user's mouth. The coating forms a peelable film shaped to the user's mouth.

EXAMPLE 6

Hydrogel Denture Adhesive Gels

Gel-type hydrogel denture adhesive is prepared by mixing 20 g of copolymer prepared by following the procedure of Example 2 and 78 g of water and 2 g of sodium alginate.

The film-type hydrogel denture adhesive is stored in a flexible tube container. The user squeezes the tube to force adhesive onto the back of a denture. The user spreads the adhesive to form a coating on the denture. The user places the denture in the user's mouth. The coating forms a peelable film shaped to the user's mouth.

EXAMPLE 7

Viscous Hydrogel Denture Adhesive Liquids

Liquid-type hydrogel denture adhesive is prepared by mixing 20 g of copolymer prepared by following the procedure of Example 1 and 50 g of water and 30 g of ethanol.

The liquid-type hydrogel denture adhesive is stored in a container of a dispenser having a pump connected by a conduit into the adhesive in the container. Liquid-type hydrogel denture adhesive is pumped by pressing the pump and the liquid-type hydrogel denture adhesive flows through a conduit, the pump and a nozzle to form a spray. Alcohol volatilizes from the spray. The volatilizing spray forms a coating on a denture. The user places the denture in the user's mouth. The coating forms a peelable film shaped to the user's mouth.

EXAMPLE 8

Viscous Hydrogel Denture Adhesive Liquids

Liquid-type hydrogel denture adhesive is prepared by mixing 15 g of copolymer prepared by following the procedure of Example 1 and 50 g of water and 35 g of ethyl alcohol.

The liquid-type hydrogel denture adhesive is stored in a container of a dispenser having a pump connected by a conduit into the adhesive in the container. Liquid-type hydrogel denture adhesive is pumped by pressing the pump and the liquid-type hydrogel denture adhesive flows through a conduit, the pump and a nozzle to form a spray. Alcohol volatilizes from the spray. The volatilizing spray forms a coating on a denture. The user places the denture in the user's mouth. The coating forms a peelable film shaped to the user's mouth.

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A method of using a denture comprising
providing a denture having an outer face,
applying a readily flowable material to said face,
said flowable material comprising volatile material and polymeric material,
volatilizing at least a portion of said volatile material from said flowable material to form a soft adhesive readily peelable water swellable solid film, said film being substantially insoluble in water, said film comprising at least 10% by weight of said polymeric material.

2. The method of claim 1 wherein said flowable material comprises less than 40% by weight of said volatile material.

3. The method of claim 1 wherein said film is effectively peelable to form a continuous film separate from said denture.

4. The method of claim 1 wherein said film has an average width of more than 0.5 mm.

5. The method of claim 1 wherein said film comprises at least 70% by weight of polymeric material.

6. The method of claim 1 wherein said film comprises at least 80% by weight of polymeric material.

7. The method of claim 1 wherein said flowable material is a gel.

8. The method of claim 1 wherein said flowable material is a liquid.

9. The method of claim 1 wherein said film comprises less than 10% by weight of water.

10. The method of claim 1 wherein said volatile material comprises at least one alcohol compound.

11. The method of claim 1 wherein applying comprises spraying.

\* \* \* \* \*